US012734187B2

(12) United States Patent
Orikoshi et al.

(10) Patent No.: US 12,734,187 B2
(45) Date of Patent: Sep. 15, 2026

(54) COMPOSITION FOR IMPROVING VASCULAR ENDOTHELIAL FUNCTION

(71) Applicant: SAN-EI GEN F.F.I., INC., Toyonaka (JP)

(72) Inventors: Hideyuki Orikoshi, Toyonaka (JP); Takafumi Imada, Toyonaka (JP)

(73) Assignee: SAN-EI GEN F.F.I., INC., Toyonaka (JP)

(*) Notice: Subject to any disclaimer, the term of this patent is extended or adjusted under 35 U.S.C. 154(b) by 862 days.

(21) Appl. No.: 17/429,113

(22) PCT Filed: Feb. 6, 2020

(86) PCT No.: PCT/JP2020/004516
§ 371 (c)(1),
(2) Date: Aug. 6, 2021

(87) PCT Pub. No.: WO2020/162532
PCT Pub. Date: Aug. 13, 2020

(65) Prior Publication Data

US 2022/0079967 A1 Mar. 17, 2022

(30) Foreign Application Priority Data

Feb. 6, 2019 (JP) ................................ 2019-020047

(51) Int. Cl.
*A61K 31/7048* (2006.01)
*A61P 9/14* (2006.01)

(52) U.S. Cl.
CPC ............ *A61K 31/7048* (2013.01); *A61P 9/14* (2018.01)

(58) Field of Classification Search
CPC .................................................. A61K 31/7048
See application file for complete search history.

(56) References Cited

U.S. PATENT DOCUMENTS

| | | | | |
|---|---|---|---|---|
| 2004/0197279 | A1* | 10/2004 | Bleckmann | A61K 8/342 424/59 |
| 2006/0011858 | A1* | 1/2006 | Engelmann | G02B 21/0076 250/458.1 |
| 2008/0182893 | A1* | 7/2008 | Nishizawa | A61K 31/7048 514/456 |

FOREIGN PATENT DOCUMENTS

| | | | | | |
|---|---|---|---|---|---|
| JP | H01-213293 | A | | 8/1989 | |
| JP | 2008-255075 | A | | 10/2008 | |
| JP | 2010-037319 | A | | 2/2010 | |
| JP | 4505707 | B2 | * | 7/2010 | A44B 11/263 |
| JP | 201025520 | A | * | 9/2010 | |
| JP | 2010215520 | A | * | 9/2010 | |
| JP | 2014097987 | | * | 5/2014 | |
| JP | 2014097987 | A | * | 5/2014 | |
| WO | WO 2006/095675 | A | | 9/2006 | |
| WO | WO 2006/132223 | A | | 12/2006 | |

OTHER PUBLICATIONS

Parker et al., "Deep forehead wrinkles could be a sign of heart disease, study says", The Atlanta Journal-Constitution, Aug. 28, 2018. (Year: 2018).*
International Preliminary Report on Patentability issued Aug. 10, 2021 in International Application No. PCT/JP2020/004516.
International Search Report mailed Mar. 17, 2020 in International Application No. PCT/JP2020/004516.
Written Opinion mailed Mar. 17, 2020 International Application No. PCT/JP2020/004516.
Notice of Reasons for Refusal dated Jun. 2, 2022 in Japanese Application No. 2020-571253.
Joannides et al. Nitric Oxide Is Responsible for Flow-Dependent Dilatation of Human Peripheral Conduit Arteries in vivo, American Heart Association Circulation, , vol. 91, Issue 5, pp. 314-1319, 1995.
Osawa et al., "Development and Applications of Natural Ingredients that Improve Blood Flow", pp. 63-72, 2018.
Bondonno, N. P. et al., Enzymatically modified isoquercitrin improves endothelial function in volunteers at risk of cardiovascular disease, British Journal of Nutrition, vol. 123, No. 2, pp. 182-189, particularly, abstract, 2019.
International Search Report mailed on Mar. 17, 2003 in application PCT/JP2020/004516.
Bondonno et. al., Acute effects of quercetin-3-gulucoside on endothelial function and blood pressure: a randomized dose-response study, Am J Clin Nutr, vol. 104, pp. 97-103, 2016.
Valentova, et al., Isoquercitrin: Pharmacology, toxicology, and metabolism, Food and Chemical Toxicology, vol. 68, pp. 267-282, 2014.
Extended European Search Report dated Oct. 17, 2022 in EP Application No. 20752026.3.
Office Action dated Jul. 1, 2024 in European Patent Application No. 20 752 026.3, 6 pages.
Flammer et al., "The Assessment of Endothelial Function From Research Into Clinical Practice." Circulation, 2012, 126: 753-767.
Thijssen et al., "Assessment of flow-mediated dilation in humans: a methodological and physiological guideline." Am J. Physiol. Heart Circ. Physiol., 2011, 300: H2-H12.

* cited by examiner

*Primary Examiner* — Traviss C Mcintosh, III
(74) *Attorney, Agent, or Firm* — Knobbe, Martens, Olson & Bear, LLP

(57) ABSTRACT

A composition for improving a vascular endothelial function contains enzyme-treated isoquercitrin. Furthermore, The composition can be provided in a food or a medication that contains the enzyme-treated isoquercitrin. Improving vascular endothelial function can result in adjustment of blood flow, vasodilation, improvement in blood pressure adjustment function, prevention of arteriosclerosis, or reduction of risk of arteriosclerosis.

5 Claims, 1 Drawing Sheet

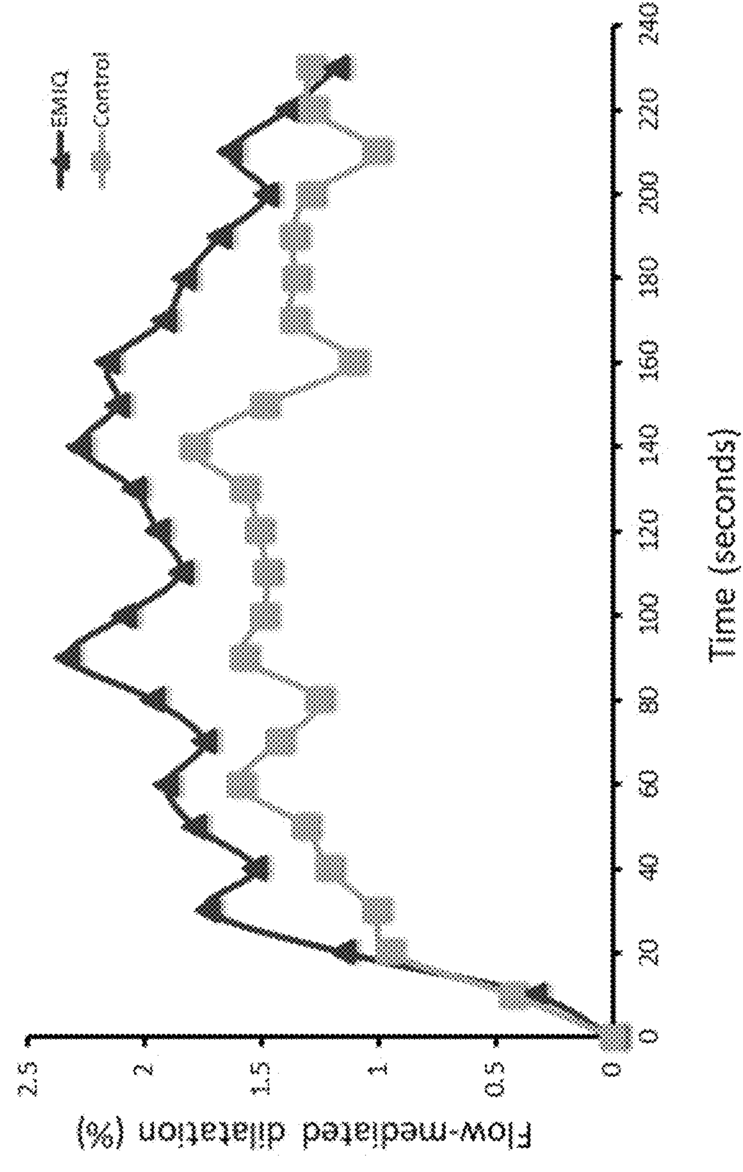
Flow-mediated dilatation (%)
Time (seconds)
EMIQ
Control
0
0.5
1
1.5
2
2.5
0
20
40
60
80
100
120
140
160
180
200
220
240

COMPOSITION FOR IMPROVING VASCULAR ENDOTHELIAL FUNCTION

PRIORITY AND CROSS REFERENCE TO RELATED APPLICATIONS

This application is the U.S. National Stage Application under 35 U.S.C. § 371 of International Application No. PCT/JP2020/004516, filed Feb. 6, 2020, designating the U.S. and published as WO 2020/162532 A1 on Aug. 13, 2020, which claims the benefit of Japanese Patent Application No. JP 2019-020047, filed Feb. 6, 2019. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to a composition for improving vascular endothelial function, and more particularly to a composition for improving vascular endothelial function containing α-glucosyl-isoquercitrin.

BACKGROUND ART

In Japan, circulatory diseases including cerebrovascular diseases and ischemic heart diseases are one of major causes of death. Furthermore, a circulatory disease not only causes death, but also leaves a sequelae even when the disease does not lead to death, and there are many cases where a person suffers from the same.

In particular, stroke is a major factor of becoming bedridden and also a major social problem. Therefore, improvement in mortality and morbidity of circulatory diseases is required.

It has been clarified that lifestyle habits are deeply involved in the onset of circulatory diseases such as stroke. Therefore, prevention measures by improving dietary habits and the like, taking effective supplements and the like are important.

On the other hand, it is considered effective to improve vascular endothelial function in a risk measure for circulatory diseases, and the risk is estimated by quantitative measurement of the vascular endothelial function. As a method of examining the vascular endothelial function, measurement of flow-mediated vasodilation (FMD) which is an arterial dilation response to shear stress based on a change in blood flow is used in clinical medicine (Non-Patent Documents 1 and 2).

PRIOR ART DOCUMENTS

Patent Document

Non-Patent Document 1: Joannides R, Haefeli W E, Linder L, Richard V, Bakkali E H, Thuillez C, Luscher T F. Nitric oxide is responsible for flow-dependent dilatation of human peripheral conduit arteries in vivo. Circulation. 1995; 91:1314-1319

Non-Patent Document 2: Toshihiko Osawa et al., "Development and Applications of Natural Ingredients that Improve Blood Flow", pp. 63-72, 2018

SUMMARY OF THE INVENTION

An object of the present invention is to provide a composition for improving vascular endothelial function.

The present inventors have focused on α-glucosyl-isoquercitrin or a mixture thereof that is generally known as enzyme-treated isoquercitrin, and have found that such a compounds have actions of significantly improving function of a blood vessel, and have completed the present invention based on such findings.

The present invention includes the following aspects:

Item 1.

A composition for improving vascular endothelial function containing as an active ingredient one kind or two or more kinds of α-glucosyl-isoquercitrin in which n is 2 to 11; or a mixture of isoquercitrin in which n is 1 and one kind or two or more kinds of α-glucosyl-isoquercitrin in which n is 2 to 11, represented by the following formula:

[Formula 1]

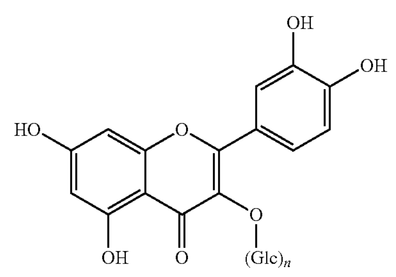

wherein Glc represents a glucose residue, and n represents an integer of 1 to 11.

Item 2.

The composition for improving vascular endothelial function according to item 1, for improving vascular endothelial contraction and/or dilation function.

Item 3.

The composition for improving vascular endothelial function according to item 1 or 2, wherein the improvement in vascular endothelial function is adjustment of blood flow, vasodilation, improvement in blood pressure adjustment function, prevention of arteriosclerosis, or reduction of risk of arteriosclerosis.

Item 4.

The composition for improving vascular endothelial function according to any one of items 1 to 3, for administering one kind or two or more kinds of α-glucosyl-isoquercitrin in which n is 2 to 11; or a mixture of isoquercitrin in which n is 1 and one kind or two or more kinds of α-glucosyl-isoquercitrin in which n is 2 to 11, represented by the above formula, at 0.1 to 100 mg/kg per dose.

Item 5.

A food and drink composition, a pharmaceutical composition, or a feed for improving vascular endothelial function, comprising:

a composition for improving vascular endothelial function containing one kind or two or more kinds of α-glucosyl-isoquercitrin in which n is 2 to 11; or a mixture of isoquercitrin in which n is 1 and one kind or two or more kinds of α-glucosyl-isoquercitrin in which n is 2 to 11, represented by the following formula:

[Chemical Formula 2]

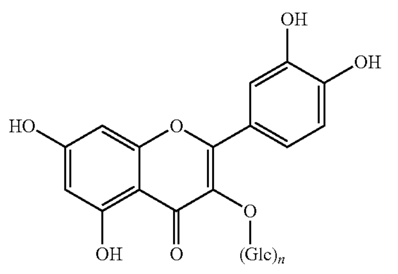

wherein Glc represents a glucose residue, and n represents an integer of 1 to 11.

According to the present invention, it is possible to provide a composition for improving vascular endothelial function containing α-glucosyl-isoquercitrin as an active ingredient.

BRIEF DESCRIPTION OF THE DRAWINGS

FIG. 1 is a graph showing evaluation results of FMD by compositions according to Examples of the present invention.

DETAILED DESCRIPTION

Unless otherwise limited, the steps, processes, or operations described herein may be performed at room temperature. In the present specification, room temperature means a temperature within a range of 10 to 40° C.

[Composition for Improving Vascular Endothelial Function]

(α-Glucosyl-isoquercitrin)

In the present invention, a mixture of α-glucosyl-isoquercitrin or the like that falls within the following definition is also referred to as enzyme-treated isoquercitrin.

That is, in the present invention, the term "enzyme-treated isoquercitrin" is referred, it is a compound represented by the following formula or a mixture thereof, that is one kind or two or more kinds of α-glucosyl-isoquercitrin in which n is 2 to 11; or a mixture of isoquercitrin in which n is 1 and one kind or two or more kinds of α-glucosyl-isoquercitrin in which n is 2 to 11.

[Formula 3]

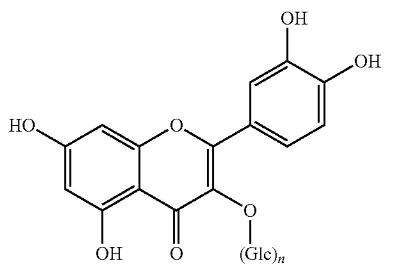

wherein Glc represents a glucose residue, and n represents an integer of 1 to 11.

Here, it is preferably, but not limited to, the two or more kinds of α-glucosyl-isoquercitrin in which n is 2 to 11; or the mixture of isoquercitrin in which n is 1 and one kind or two or more kinds of α-glucosyl-isoquercitrin in which n is 2 to 11 is a mixture of two or more kinds of compounds in which n is selected from 1 to 7. Note that α-glucosyl-isoquercitrin in which n is 1 is also simply referred to as "isoquercitrin". In the present invention, the enzyme-treated isoquercitrin is preferably not a single compound of n=1.

Here, the two or more kinds of α-glucosyl-isoquercitrin in which n is 2 to 11; or the mixture of isoquercitrin in which n is 1 and one kind or two or more kinds of α-glucosyl-isoquercitrin in which n is 2 to 11 may be a mixture containing a compound or compounds with n=2 to 11 or n=1 to 11 in any proportions. In the case of a mixture, for example, compounds containing compounds of n=1 to n=11 in equal proportions may be used. For example, it is preferably a mixture containing about 20 to 40% by mass of the compound of n=1 and about 10 to 30% by mass of the compound of n=2 in a whole mixture. In addition, a mixture containing about 20 to 40% by mass of a compound of n=1, about 10 to 30% by mass of a compound of n=2, about 10 to 40% by mass of a compound of n=3, about 5 to 20% by mass of a compound of n=4, about 5 to 15% by mass of a compound of n=5, about 3 to 10% by mass of a compound of n=6, and about 2 to 8% by mass of a compound of n=7 in the whole mixture, or a mixture containing about 20 to 40% by mass of a compound of n=1, about 10 to 30% by mass of a compound of n=2, about 10 to 40% by mass of a compound of n=3, about 5 to 20% by mass of a compound of n=4, and about 5 to 15% by mass of a compound of n=5, about 3 to 10% by mass of a compound of n=6, about 2 to 8% by mass of a compound of n=7, about 1 to 5% by mass of a compound of n=8, about 0.2 to 4% by mass of a compound of n=9, about 0.1 to 2% by mass of a compound of n=10, and about 0.1 to 2% by mass of a compound of n=11 in the whole mixture.

(Preparation Method)

The enzyme-treated isoquercitrin of the present invention can be obtained by, but is not limited to, treating rutin with an enzyme. For example, rutin may be converted into isoquercitrin by a hydrolase, and this isoquercitrin may be further reacted with a glycosyltransferase in the presence of dextrin to form enzyme-treated isoquercitrin.

In the present invention, it is preferable to use enzyme-treated isoquercitrin containing at least 60% by mass or more of α-glucosyl-isoquercitrin in terms of the amount of rutin. The reason why α-glucosyl-isoquercitrin content in enzyme-treated isoquercitrin in terms of rutin is shown is that molar absorbance coefficients of α-glucosyl-isoquercitrin and rutin at a wavelength of 351 nm are the same, and rutin is more easily available than α-glucosyl-isoquercitrin. Therefore, in the art, it is commonly used to quantify the α-glucosyl-isoquercitrin content in enzyme-treated isoquercitrin as rutin by ultraviolet-visible spectrophotometry using rutin as a standard sample.

Specifically, the α-glucosyl-isoquercitrin content in enzyme-treated isoquercitrin can be calculated as an amount in terms of rutin by the following quantitative method described in the column of "enzyme-treated isoquercitrin" in Japan's Specifications and Standards for Food Additives, 9th Edition (Ministry of Health, Labour and Welfare).

(Quantitative Method)

(i) Enzyme-treated isoquercitrin (subject sample) is dried, and about 50 mg of the dried isoquercitrin is precisely weighed and dissolved in water to make exactly 100 ml. If necessary, the solution is filtered. 4 ml of this solution was accurately weighed, and a phosphoric acid solution (an aqueous solution obtained by dissolving 1 g of phosphoric acid in water to make the total amount 1000 ml, the same applies hereinafter) is added thereto to make exactly 100 ml, which is used as a test solution.

(ii) Separately, rutin for quantification is dried at 135° C. for 2 hours, and about 50 mg thereof is weighed precisely and dissolved in methanol to make exactly 100 ml. 4 ml of this solution is accurately weighed, and a phosphoric acid solution is added thereto to make exactly 100 ml, which is used as a standard solution.

(iii) For the test solution and the standard solution, absorbances $A_T$ and $A_S$ at a wavelength of 351 nm are measured using a phosphoric acid solution as a control by ultraviolet-visible spectrophotometry, and the content of α-glucosyl-isoquercitrin as rutin is determined by the following equation.

Content of α-glucosyl-isoquercitrin(as the content of rutin[$C_{27}H_{30}O_{16}$]=(amount of rutin for quantification (g)/amount of sample (g))×($At/As$)×100 (mass %) [Equation 1]

Furthermore, the enzyme-treated isoquercitrin of the present invention can generally be prepared by adding glucose to a mixture of isoquercitrin and starch or dextrin using cyclodextrin glucosyltransferase (for example, JP-A-1-213293, etc.). Moreover, the enzyme-treated isoquercitrin is generally obtained by enzymatic degradation of rutin, but can also be obtained by other known methods (for example, degradation of rutin, extraction and isolation from plants, glycosylation of quercetin, etc.). In addition, a formulation containing enzyme-treated isoquercitrin can be conveniently obtained commercially, and examples thereof include "San Emic R-20" manufactured by San-Ei Gen F.F.I., Inc. Note that "San Emic" is a registered trademark of San-Ei Gen F.F.I., Inc.

(Improvement in Vascular Endothelial Function)

The effect of improving vascular endothelial function in the present invention means having an effect of improving contraction/dilation function of the vascular endothelium, and can contribute to prevention, improvement or alleviation of a disease or symptom caused by a deterioration of vascular endothelial function due to a circulatory system disease, particularly arteriosclerosis, a deterioration of blood vessel elasticity or the like, or a symptom of diseases related to these diseases.

Vascular endothelial cells have an effect of dilating blood vessel diameter in response to nitric oxide (NO) produced in response to shear stress due to increased or decreased blood flow. Therefore, for example, based on the amount of nitric oxide generated from the vascular endothelial cells, how much the artery spreads after opening (after avascularization) after compressing the arm or the like can be detected by an examination using ultrasound or the like.

The degree of improvement in vascular endothelial function can be quantitatively evaluated as, specifically, rate of increase in blood vessel diameter, that is, flow-mediated dilatation (FMD value (%)). The FMD value is obtained by the following Equation.

% FMD(Vasodilation rate)=(Maximum dilated vessel diameter−vessel diameter at rest)/vessel diameter at rest×100 [Equation 2]

Here, the maximum dilated blood vessel diameter is a post-avascularization blood vessel diameter, and the vessel diameter at rest is a pre-avascularization blood vessel diameter.

The larger the FMD value, it is evaluated as a blood vessel having higher responsive function and high flexibility, and the lower the FMD value, it is evaluated as a blood vessel having low flexibility. Furthermore, it is known that the FMD value (%) correlates with onset risk of a circulatory system disease. That is, it is said that the FMD value (%) of a patient with a vascular disease such as arteriosclerosis and a person who may have the vascular disease is lower than that of a healthy person.

In the present invention, the action of improving vascular endothelial function and the action of ameliorating vascular endothelial function are each used for a healthy person, a patient with a vascular disease such as arteriosclerosis, and a person who may have the vascular disease. For example, when the FMD value of a healthy person has been increased, it can be determined that the vascular endothelial function of the person has been improved. In addition, when the FMD value of a patient with a vascular disease such as arteriosclerosis and a person who may have the vascular disease has been increased, it can be determined that the vascular endothelial function of the person has been improved.

The content of the enzyme-treated isoquercitrin contained in the composition for improving vascular endothelial function of the present invention can be appropriately adjusted according to the type and moisture content of the composition, and the purpose and use. For example, the content of enzyme-treated isoquercitrin contained in the composition for improving vascular endothelial function of the present invention is preferably 0.01 to 100% by mass. The content is more preferably 1 to 95% by mass, further preferably 5 to 90% by mass, and still more preferably 10 to 85% by mass.

In the present specification, the content of enzyme-treated isoquercitrin is indicated as the content (as rutin [$C_{27}H_{30}O_{16}$]) (% by mass) of α-glucosyl-isoquercitrin contained therein as described above unless otherwise specified. Therefore, in the invention of the present application (present specification), "1 part by mass of enzyme-treated isoquercitrin" means an amount when the amount of α-glucosyl-isoquercitrin contained in the enzyme-treated isoquercitrin is converted into the amount of rutin [$C_{27}H_{30}O_{16}$] to be 1 part by mass.

The composition for improving vascular endothelial function of the present invention may contain a diluent, a carrier or other additives as components other than the enzyme-treated isoquercitrin.

The diluent or carrier is not particularly limited, and examples thereof include saccharides such as sucrose, glucose, dextrin, starches, trehalose, lactose, maltose, starch syrup, or liquid sugar; alcohols such as ethanol, propylene glycol, and glycerin; sugar alcohols such as sorbitol, mannitol, xylitol, erythritol, and maltitol; polysaccharides such as gum arabic, gum ghatti, xanthan gum, carrageenan, guar gum, gellan gum, and celluloses; or water.

The composition for improving vascular endothelial function of the present invention can exhibit a function of improving vascular endothelial function when it is inoculated or administered to an animal including human. It is known that the vascular endothelial function is closely related to the onset risk of arteriosclerosis, hypertension, cardiovascular disease, arteriosclerosis, and the like. By improving vascular endothelial function, flexibility of the blood vessel can be secured, and the blood flow can be adjusted. Furthermore, arteriosclerosis can be prevented, and hypertension can be prevented. The composition for improving vascular endothelial function of the present invention can be used for prevention or treatment of diseases such as, but not limited to, arteriosclerosis, diabetes, hypertension, or dyslipidemia, as well as metabolic syndrome, obesity, insulin resistance, impaired glucose tolerance, diabetic peripheral neuropathy, diabetic nephropathy, diabetic retinopathy, diabetic macroangiopathy, cardiovascular disease, atherosclerosis, heart failure, myocardial infarction, coronary artery disease, and cerebrovascular disease. Further, it can also be used for improvement of dry spots, wrinkles, sagging of the skin, and improvement of swelling, improvement of cold sensitivity and shoulder stiffness, improvement of scalp environment, and the like. Furthermore, the composition for improving vascular endothelial function of the present invention is also effective for healthy subjects, particularly from a prophylactic viewpoint.

The composition for improving vascular endothelial function of the present invention is excellent in the action of improving vascular endothelial function, and can lead to alleviation of symptoms and the like in a short time in some cases.

For example, it has been reported that isoquercitrin, which is one of common flavonoids, does not affect the FMD value and blood pressure even when administered to human (Nicola P Bondonno et. al, (2016). Accute effects of que4rcetin-3-gulucoside on endothelial function and blood pressure: a randomized dose-response study. Am J Clin Nutr, 104, 97-103). The report also discloses that increasing the dosage of isoquercitrin does not have these effects.

(Food and Drink Composition, Pharmaceutical Composition, or Feed)

In the present invention, the enzyme-treated isoquercitrin may be contained in a pharmaceutical composition, quasi-drug, food and drink composition for humans or animals, or a feed. Alternatively, the enzyme-treated isoquercitrin can be first made into a material or formulation (composition for improving vascular endothelial function) to be used by being blended in the pharmaceutical composition, quasi-drug, food and drink composition, or feed, and then blended in these. The composition containing the enzyme-treated isoquercitrin of the present invention can exhibit a function of improving vascular endothelial function as a food and drink composition, a pharmaceutical composition, a feed, or the like. It is known that the vascular endothelial function is closely related to the onset risk of arteriosclerosis, hypertension, cardiovascular disease, arteriosclerosis, and the like. By improving vascular endothelial function, flexibility of the blood vessel can be secured, and the blood flow can be adjusted. Furthermore, arteriosclerosis can be prevented, and hypertension can be prevented. The composition containing enzyme-treated isoquercitrin of the present invention can be used for prevention or treatment of diseases such as, but not limited to, arteriosclerosis, diabetes, hypertension, or dyslipidemia, as well as metabolic syndrome, obesity, insulin resistance, impaired glucose tolerance, diabetic peripheral neuropathy, diabetic nephropathy, diabetic retinopathy, diabetic macroangiopathy, cardiovascular disease, atherosclerosis, heart failure, myocardial infarction coronary artery disease, and cerebrovascular disease. Furthermore, the composition of the present invention is also effective for healthy subjects, particularly from a prophylactic viewpoint. For example, but not limited to, the composition of the present invention can be suitably used for an action of lowering blood cholesterol of a person with high blood cholesterol, a function suitable for a person with high blood pressure, a function of suppressing an increase in neutral fat in blood, a function of supporting healthy blood pressure of a person with high blood pressure, a function of supporting a person who cares about blood cholesterol, a function of maintaining healthy blood flow, a function of maintaining healthy peripheral blood flow, a function of maintaining body temperature, blood pressure improvement, blood pressure maintenance, improvement of dryness, wrinkles and sagging of the skin, improvement of scalp environment, and the like.

<Food and Drink Composition>

The food and drink composition of the present invention includes, as necessary, foods, functional foods, foods for patients, and foods for specified health uses, which are labeled to improve vascular endothelial function.

Examples of the form of the food and drink composition include beverages such as milk beverages, lactic acid bacteria beverages, carbonated beverages, fruit beverages (e.g., fruit juice beverages, fruit juice-containing soft beverages, fruit juice-containing carbonated beverages, and fruit pulp beverages), vegetable beverages, vegetable and fruit beverages, alcoholic beverages such as liqueur, coffee beverages, powder beverages, sports beverages, and supplement beverages;

- tea beverages such as black tea beverages, green tea, and blended tea (note that beverages and tea beverages are included in "beverage");
- puddings such as custard pudding, milk pudding, and pudding with fruit juice, and desserts such as jelly, bavarian cream, and yogurt;
- frozen confectionery such as ice cream, ice milk, lact ice, and frozen confectionery;
- gums such as chewing gum and bubble gum (e.g., plate gum, sugar-coated tablet gum);
- chocolates such as coated chocolate (e.g., marble chocolate, etc.) and chocolate with flavor (e.g., strawberry chocolate, blueberry chocolate, melon chocolate, etc.);
- candies such as hard candies (e.g., bonbon, butter ball, marble, etc.), soft candies (e.g., caramel, nougat, gummy candy, marshmallow, etc.), sugar-coated candies, drops, and toffies;
- confectionery such as cookies and biscuits;
- soups such as consommé soup and potage soup;
- liquid seasonings such as separate dressing, non-oil dressing, ketchup, dipping sauce, and sauce;
- jams such as strawberry jam, blueberry jam, marmalade, apple jam, apricot jam, preserve, and syrup;
- fruit liquor such as red wine;
- processing fruits such as cherry, apricot, apple, strawberry, and peach preserved in syrup;
- agricultural processed products such as pickled vegetables;
- processed marine products such as fish paste products; and
- cereal-processed food such as bread, noodles (including non-fried noodles), steamed bun dough, and rice.

Examples of the food and drink composition also include semi-finished products and intermediate products of these products, and the like. Furthermore, nutritional compositions such as tablets, capsules and syrups, which are in the same form as pharmaceuticals, are also included in examples of the food and drink composition.

To the food and drink composition, one used as a food additive can also be added in the same manner as usual food and drink. Particularly suitable additives for combination with a flavor of the enzyme-treated isoquercitrin include, but are not limited to, high-intensity sweeteners such as acesulfame K, sucralose, aspartame, advantame, saccharin, neotame, thaumatin, monellin, monatin, luohanguo extract, licorice extract, glycyrrhizin, *stevia* extract, *stevia* enzyme-treated product, rebaudioside A, and stevioside. In addition, acids, fatty acids, saccharides, sugar alcohols, alcohols, antioxidants, proteins, peptides, amino acids, vitamins, minerals, and thickening stabilizer; auxiliaries such as chelating agent; perfume; spice extract; antiseptic; preservative; pH adjuster; stabilizer; surfactant or the like can be contained.

The content of the enzyme-treated isoquercitrin contained in the food and drink composition of the present invention is preferably 0.01 to 100% by mass, further preferably 0.1 to 50% by mass, and still more preferably 0.2 to 25% by mass.

<Pharmaceutical Composition>

The composition of the present invention may be a pharmaceutical composition for improving vascular endothelial function. Examples of a dosage form of the pharmaceutical composition (including quasi-drug) include tablets (including troches and chewables), pills, capsules, granules, powders, syrups, intravenous injections, intramuscular injections, suppositories, inhalants, transdermal absorbents, eye drops, nasal drops, and the like.

Examples of the "quasi-drug" include nutritional auxiliaries, various supplements, dentifrice agents, mouth fresheners, odor preventing agents, hair growth tonics, hair tonics, moisturizers for skin, and the like.

In addition, in order to prepare pharmaceutical preparations of such various dosage forms, the enzyme-treated isoquercitrin can be appropriately combined with other pharmaceutically acceptable excipients, binders, extenders, disintegrants, surfactants, lubricants, dispersants, buffers, preservatives, flavoring agents, perfumes, coatings, carriers, diluents, other medicinal ingredients, and the like. Among these administration forms, a preferred form is oral administration, and an oral liquid formulation can be prepared by a common method by adding a flavoring agent, a buffer, a stabilizer, and the like.

The content of the enzyme-treated isoquercitrin contained in the pharmaceutical composition of the present invention is preferably 0.01 to 100% by mass, further preferably 0.1 to 50% by mass, and still more preferably 0.2 to 25% by mass.

<Feed>

The composition of the present invention may be a feed for improving vascular endothelial function. Examples of the feed include feed for small animals used for rabbits, rats, mice, and the like, and feed such as pet food used for dogs, cats, and the like, and the feed can be prepared in the same form as the above food and drink composition as long as pets can eat.

The content of the enzyme-treated isoquercitrin contained in the feed of the present invention is preferably 0.01 to 100% by mass, further preferably 0.1 to 50% by mass, and still more preferably 0.2 to 25% by mass.

(Dose, etc.)

The intake of the enzyme-treated isoquercitrin or composition for improving vascular endothelial function of the present invention or the like may vary according to the species, weight, sex, age, condition, or other factors of the subject. The dose, route, interval, and amount and interval of intake of administration can be appropriately determined by those skilled in the art, and are generally preferably 100 μg/kg body weight or more, more preferably 500 μg/kg body weight or more, further preferably 1.0 mg/kg body weight or more, preferably 100 mg/kg body weight or less, more preferably 75 mg/kg body weight or less, and further preferably 50 mg/kg body weight or less, as the enzyme-treated isoquercitrin per day for an adult. In addition, it is preferably 100 μg to 100 mg/kg body weight, more preferably 500 μg to 75 mg/kg body weight, and further preferably 1.0 mg/kg body weight to 50 mg/kg body weight.

(Administration or Intake Subject)

Administration or intake subject is not particularly limited as long as the subject is a person who needs or desires administration or intake the composition, regardless of a patient or a healthy person. A person who cares about function of blood vessels and a middle aged person are also preferable as the subject. In addition, the composition for improving vascular endothelial function of the present invention can be applied to a subject in need of blood vessel protection enhancement or a subject who desires blood vessel protection enhancement.

(Method for Producing Composition for Improving Vascular Endothelial Function, Food and Drink Composition, Pharmaceutical Composition, or Feed)

The method for producing the composition for improving vascular endothelial function, food and drink composition, pharmaceutical composition, or feed of the present invention is not limited, and they can be produced by any known method. In these production methods, the content and content amount of each component conform to the description of the composition for improving vascular endothelial function, food and drink composition, pharmaceutical composition, or feed described above.

(Method for Improving Vascular Endothelial Function, Etc.)

The present invention also relates to a method for improving vascular endothelial function by administering or ingesting a composition containing enzyme-treated isoquercitrin.

Here, the definition of vascular endothelial function improvement, the details of the related disease, the administration or intake subject, the dose, and the like conform to the content described in the section of the composition for improving vascular endothelial function.

(Use of Enzyme-Treated Isoquercitrin for Producing Composition for Improving Vascular Endothelial Function)

The present invention also relates to a use of enzyme-treated isoquercitrin for producing a composition or drug for improving vascular endothelial function. Here, the definition of vascular endothelial function improvement, the details of the related disease, the administration or intake subject, the dose, and the like conform to the content described in the section of the composition for improving vascular endothelial function.

That is, the present invention relates to:

[1]

a use of one kind or two or more kinds of α-glucosyl-isoquercitrin in which n is 2 to 11; or a mixture of isoquercitrin in which n is 1 and one kind or two or more kinds of α-glucosyl-isoquercitrin in which n is 2 to 11, represented by the following chemical formula, for production of a composition or drug for improving vascular endothelial function.

[Formula 4]

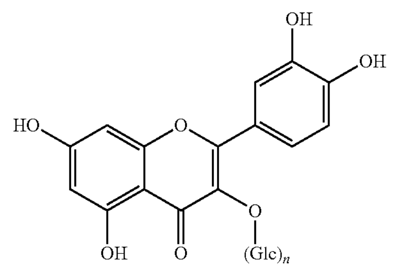

wherein Glc represents a glucose residue, and n represents an integer of 1 to 11.

[2]

The use according to [1], in which the improvement in vascular endothelial function is to improve vascular endothelial contraction and/or dilation function.

[3]

The use according to [1] or [2], in which the improvement in vascular endothelial function is adjustment of blood flow, vasodilation, improvement in blood pressure adjustment function, prevention of arteriosclerosis, or reduction of risk of arteriosclerosis.

[4]

The use according to any one of [1] to [3], in which one kind or two or more kinds of α-glucosyl-isoquercitrin in which n is 2 to 11; or a mixture of isoquercitrin in which n is 1 and one kind or two or more kinds of α-glucosyl-isoquercitrin in which n is 2 to 11, represented by the above formula is administered at 0.1 to 100 mg/kg per dose.

[5]

The use according to any one of [1] to [4], in which the composition or drug for improving vascular endothelial function is for prevention or treatment of diabetes, hypertension, dyslipidemia, metabolic syndrome, obesity, insulin resistance, impaired glucose tolerance, diabetic peripheral neuropathy, diabetic nephropathy, diabetic retinopathy, diabetic macroangiopathy, cardiovascular disease, atherosclerosis, heart failure, myocardial infarction, coronary artery disease, and cerebrovascular disease.

[6]

The use according to any one of [1] to [5], in which the composition or drug for improving vascular endothelial function is for improvement of dry spots, wrinkles, sagging of the skin, improvement of swelling, improvement of cold sensitivity and shoulder stiffness, and improvement of scalp environment.

[7]

The use according to any one of [1] to [6], in which the composition or drug for improving vascular endothelial function is for leading to alleviation of symptoms or the like in a short time.

(Composition for Improving Vascular Endothelial Function)

The present invention also includes the following aspects:

[8]

A composition for improving vascular endothelial function containing as an active ingredient one kind or two or more kinds of α-glucosyl-isoquercitrin in which n is 2 to 11; or a mixture of isoquercitrin in which n is 1 and one kind or two or more kinds of α-glucosyl-isoquercitrin in which n is 2 to 11, represented by the following formula:

[Formula 5]

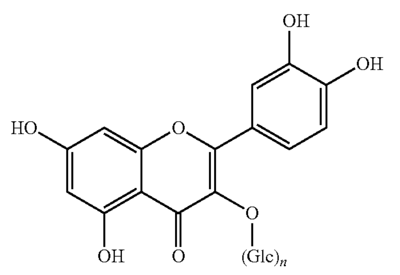

wherein Glc represents a glucose residue, and n represents an integer of 1 to 11.

[9]

The composition for improving vascular endothelial function according to [8], in which the composition contains the mixture at a ratio of 30% by mass in terms of α-glucosyl-isoquercitrin, and contains maltodextrin as another component.

[10]

The composition for improving vascular endothelial function according to [8] or [9], in which the mixture is administered as α-glucosyl-isoquercitrin at 1.0 mg/kg body weight to 50 mg/kg body weight per dose.

[11]

The composition for improving vascular endothelial function according to any one of [8] to [10], for leading to alleviation of symptoms or the like in a short time.

[12]

The composition for improving vascular endothelial function according to any one of [8] to [11], in which plasma quercetin concentration is increased by single dose.

[13]

The composition for improving vascular endothelial function according to any one of [8] to [12], which is for prevention or treatment of diabetes, hypertension, dyslipidemia, metabolic syndrome, obesity, insulin resistance, impaired glucose tolerance, diabetic peripheral neuropathy, diabetic nephropathy, diabetic retinopathy, diabetic macroangiopathy, cardiovascular disease, atherosclerosis, heart failure, myocardial infarction, coronary artery disease, and cerebrovascular disease.

[14]

The composition for improving vascular endothelial function according to any one of [8] to [13], which is for improvement of dry spots, wrinkles, and sagging of the skin, improvement of swelling, improvement of cold sensitivity and shoulder stiffness, and improvement of scalp environment.

Examples

Hereinafter, the present invention will be described with reference to Examples, but the scope of the present invention is not limited thereto. Unless otherwise specified, numerical values of "%", "number of parts" and the like represent numerical values on a mass basis.

(Composition Containing Enzyme-Treated Isoquercitrin)

In evaluating the following vascular endothelial function improvement, San Emic (registered trademark) R-20: manufactured by San-Ei Gen F.F.I., Inc.) (containing enzyme-treated isoquercitrin in a ratio of 30% by mass in terms of α-glucosyl-isoquercitrin, and containing maltodextrin as another component) was used.

(Method for Evaluating Vascular Endothelial Function)

Whether administration of enzyme-treated isoquercitrin improves vascular function in human volunteers was evaluated.

Specifically, a control crossover study was performed randomly in 25 healthy volunteers with at least one risk factor for cardiovascular disease. There was a minimum of one week of drug withdrawal during the study days. The test subjects received enzyme-treated isoquercitrin (intake of 4.89 mg/kg body weight as α-glucosyl-isoquercitrin or placebo control). Maltodextrin was used as a carrier for the enzyme-treated isoquercitrin, and maltodextrin alone was used as a placebo control. The product was dissolved in 200 ml of water and administered orally. Endothelial function and blood pressure were evaluated 2 hours before and after administration.

<FMD Measurement and Blood Pressure Measurement>

Before measuring FMD, blood pressure of the subject was measured using an electronic sphygmomanometer (Dinamap 1846SX/P).

For FMD measurement, in order to stop blood flow in the brachial artery, pressure (blood pressure+40 mmHg) was applied to a forearm part for 5 minutes using a cuff of a mercury sphygmomanometer. The pressure was then released by contracting the cuff, and the brachial artery was monitored simultaneously by ultrasound diagnostic equipment (Acuson Aspen 128, Acuson Corporation). Based on the arterial diameter measurements, the FMD expansion rate (% FMD) was calculated.

<Statistical Processing>

Statistical processing was performed by SPSS15.0 software (SPSS), and analysis values are expressed as mean±standard deviation. Differences in mean values were evaluated by complex model variance analysis, followed by Bonferroni multiple comparison test.

(Evaluation Results of Vascular Endothelial Function)

Administration of the composition containing enzyme-treated isoquercitrin prepared in Examples resulted in a significant improvement in vascular function measured as rate of increase in blood vessel diameter (FMD value) (P<0.04, FIG. 1). That is, FIG. 1 shows a change in FMD over 240 seconds at 2 hours after administration. The results are presented as mean values (n=24).

The subjects had a mean age of 64 years, evidence of cardiovascular risk factors and endothelial dysfunction (peak FMD<3%). Administration of the compositions of Examples could improve FMD. Plasma quercetin was increased 10 fold after enzyme-treated isoquercitrin administration.

From these results, it was concluded that enzyme-treated isoquercitrin at a single dose increases plasma quercetin concentration and causes significant improvement in vascular function in subjects.

Such effects are surprising when compared to the reports that administration of isoquercitrin to humans has no effect on FMD.

Formulation examples are shown below.

TABLE 1

(Coffee beverage formulation example) (% by mass)

| | Comparative Formulation Example 1 | Formulation Example 1 |
|---|---|---|
| Sucralose | 0.0014 | 0.0014 |
| Coffee flavor | 0.1 | 0.1 |
| Enzyme-treated isoquercitrin formulation** | — | 1.5 |
| Gluconic acid | 0.02 | 0.02 |
| Total with water | 100 | 100 |

TABLE 2

(Tablet formulation example) (% by mass)

| | Comparative Formulation Example 2 | Formulation Example 2 |
|---|---|---|
| Sorbitol | 97.1 | 82.1 |
| High-intensity sweetener formulation* | 0.15 | 0.15 |
| Powder flavor | 0.75 | 0.75 |
| Enzyme-treated isoquercitrin formulation** | | 15 |
| Sucrose fatty acid ester | 2 | 2 |
| Total | 100 | 100 |

TABLE 3

(Feed formulation example)

| Basic raw material | Blending ratio (parts by mass) |
|---|---|
| Enzyme-treated isoquercitrin formulation** | 5 |
| Corn flour | 549 |
| Soybean cake | 76 |
| Gluten meal | 70 |
| Meat powder | 225 |
| Beef tallow | 35 |
| Fish powder | 10 |
| Calcium carbonate | 5 |
| Calcium phosphate | 9 |
| Salt | 5 |
| Amino acid | 4 |
| Vitamin and mineral mix | 7 |
| Total | 1000 |

The components in the tables are as follows.

*High-intensity sweetener formulation: "Sunsweet (registered trademark) SA-8020"

(containing 24% by mass sucralose, 18% by mass acesulfame potassium, and 58% by mass reduced palatinose) manufactured by San-Ei Gen F.F.I., Inc.

**Enzyme-treated isoquercitrin formulation: "San Emic (registered trademark) R-20"

(containing 20% by mass α-glucosyl-isoquercitrin (in terms of rutin), dextrin as another component) manufactured by San-Ei Gen F.F.I., Inc.

What is claimed is:

1. A method for improving or alleviating a condition in a subject in need thereof, the method comprising:

administering to the subject orally one or more kinds of α-glucosyl-isoquercitrin, or a mixture of isoquercitrin and one or more kinds of α-glucosyl-isoquercitrin, wherein the condition is selected from the group consisting of dry spots, wrinkles, sagging, swelling, sensitivity to cold, and stiff shoulders, wherein said improving or alleviating the condition is achieved by increasing a flow-mediated vasodilation (FMD) value, wherein the α-glucosyl-isoquercitrin is represented by the following formula:

[Formula 1]

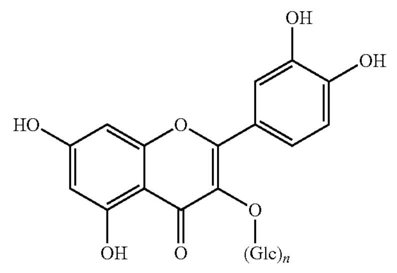

wherein Glc represents a glucose residue, and n represents an integer of 2 to 11.

2. The method of claim 1, wherein the one or more kinds of α-glucosyl-isoquercitrin is administered at 1.0 mg/kg body weight to 50 mg/kg body weight per dose.

3. The method of claim 1, wherein the mixture of isoquercitrin and one or more kinds of α-glucosyl-isoquercitrin is administered at 1.0 mg/kg body weight to 50 mg/kg body weight per dose.

4. The method of claim 1, wherein the subject is middle-aged and older subjects with at least one risk factor for cardiovascular disease.

5. The method of claim 1, wherein the condition is selected from the group consisting of swelling, sensitivity to cold, and stiff shoulders.

* * * * *